United States Patent
Chen et al.

(10) Patent No.: US 8,222,473 B1
(45) Date of Patent: Jul. 17, 2012

(54) ISOMERIZATION OF LIGHT PARAFFINS

(75) Inventors: Cong-Yan Chen, Kensington, CA (US);
Xiaoying Ouyang, Goleta, CA (US);
Tracy M. Davis, Novato, CA (US);
Stacey I. Zones, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 13/334,844

(22) Filed: Dec. 22, 2011

(51) Int. Cl.
*C07C 5/27* (2006.01)

(52) U.S. Cl. ......................................... 585/739; 585/751

(58) Field of Classification Search .................. 585/739, 585/751
See application file for complete search history.

(56) References Cited

U.S. PATENT DOCUMENTS

| | | | |
|---|---|---|---|
| 4,374,296 A * | 2/1983 | Haag et al. | 585/739 |
| 7,651,603 B2 | 1/2010 | Zones et al. | |
| 7,713,512 B2 | 5/2010 | Zones et al. | |
| 2011/0130610 A1 | 6/2011 | Chen et al. | |

* cited by examiner

*Primary Examiner* — Thuan Dinh Dang
(74) *Attorney, Agent, or Firm* — Terrence M. Flaherty

(57) ABSTRACT

A process for isomerizing light paraffins using a catalyst comprising an STI-type zeolite and at least one Group VIII metal. It has been found that the catalyst can selectively convert $C_6$ paraffins into the more favorable higher octane $C_6$ isomer, namely 2,3-dimethylbutane (RON=105), over the less favorable $C_6$ isomer, namely octane 2,2-dimethylbutane (RON=94).

10 Claims, No Drawings

ISOMERIZATION OF LIGHT PARAFFINS

TECHNICAL FIELD

The application generally relates to a process for isomerizing light paraffins by using a catalyst comprising an STI-type zeolite and at least one Group VIII metal. Such catalysts show high selectivity in the conversion of n-hexane to the higher octane $C_6$ isomer 2,3-dimethylbutane over the lower octane $C_6$ isomer 2,2-dimethylbutane.

BACKGROUND

Modern automobile engines require high octane gasoline for efficient operation. Previously, lead and oxygenates, such as methyl-t-butyl ether (MTBE), were added to gasoline to increase the octane number. Furthermore, several high octane components normally present in gasoline, such as benzene, aromatics, and olefins, must now be reduced. Obviously, a process for increasing the octane of gasoline without the addition of toxic or environmentally adverse substances would be highly desirable.

Gasoline is generally prepared from a number of blend streams, including light naphthas, full range naphthas, heavier naphtha fractions, and heavy gasoline fractions. The gasoline pool typically includes butanes, light straight run, isomerate, FCC cracked products, hydrocracked naphtha, coker gasoline, alkylate, reformate, added ethers, etc. Of these, gasoline blend stocks from the FCC, the reformer and the alkylation unit account for a major portion of the gasoline pool.

For a given carbon number of a light naphtha component, the shortest, most branched isomer tends to have the highest octane number. For example, the singly and doubly branched isomers of hexane, mono-methylpentane and dimethylbutane respectively, have octane numbers that are significantly higher than that of n-hexane, with dimethylbutane having the highest research octane number (RON). Likewise, the singly branched isomer of pentane, 2-methylbutane, has a significantly higher RON than n-pentane. By increasing the proportion of these high octane isomers in the gasoline pool, satisfactory octane numbers can be achieved for gasoline without additional additives.

Two types of octane numbers are currently being used, the motor octane number (MON) determined using ASTM D2700-11 ("Standard Test Method for Motor Octane Number of Spark-Ignition Engine Fuel") and the RON determined using ASTM D2699-11 ("Standard Test Method for Research Octane Number of Spark-Ignition Engine Fuel"). The two methods both employ the standard Cooperative Fuel Research (CFR) knock-test engine. Sometimes, the MON and RON are averaged, (MON+RON)/2, to obtain an octane number. Therefore, when referring to an octane number, it is essential to know which one is being discussed. In this disclosure, unless clearly stated otherwise, octane number will refer to the RON. For comparative purposes, the RON for isomers of pentane and hexane are listed in Table 1.

TABLE 1

| | RON |
|---|---|
| $C_5$ paraffins | |
| n-pentane | 62 |
| 2-methylbutane | 92 |

TABLE 1-continued

| | RON |
|---|---|
| $C_6$ paraffins | |
| n-hexane | 25 |
| 2-methylpentane | 74 |
| 3-methylpentane | 76 |
| 2,2-dimethylbutane | 94 |
| 2,3-dimethylbutane | 105 |

Gasoline suitable for use as fuel in an automobile engine should have a RON of at least 80, e.g., at least 85, or at least 90. High performance engines generally require a fuel having a RON of about 100. Most gasoline blending streams have a RON generally ranging from 55 to 95, with the majority typically falling between 80 and 90. Obviously, it is desirable to maximize the amount of dimethylbutane in light paraffins of the gasoline pool in order to increase the overall RON.

Hydroisomerization is an important refining process whereby the RON of a refinery's gasoline pool can be increased by converting straight chain normal or singly branched light paraffins into their more branched isomers. The hydroisomerization reaction is controlled by thermodynamic equilibrium. At higher reaction temperatures, the equilibrium shifts towards the lower octane isomers (e.g., from dimethylbutanes via methylpentanes to n-hexane). Since the high octane components (e.g., 2,3-dimethylbutane with a RON=105) are the target products in this process, it is desirable to develop a more active catalyst to perform this reaction at a lower temperature.

There is a need for new and improved hydrocarbon hydroisomerization catalysts and processes that provide high selectivity for producing high octane isomers of light paraffins, wherein the catalysts are also highly active, environmentally benign, and readily regenerable.

SUMMARY

There is provided a hydroisomerization process comprising contacting a hydrocarbon feed comprising predominantly normal and singly branched $C_4$ to $C_7$ paraffins, under hydroisomerization conditions, with a catalyst comprising an aluminosilicate STI-type zeolite and at least one Group VIII metal to form an isomerized product having a higher concentration of doubly and singly branched paraffins than the feed stream and having a 2,3-dimethylbutane to 2,2-dimethylbutane mole ratio of at least 1.

DETAILED DESCRIPTION

The following terms will be used throughout the specification and will have the following meanings unless otherwise indicated.

"Hydroisomerization" refers to a process in which paraffins are isomerized to their more branched counterparts in the presence of hydrogen over a catalyst. Hydroisomerization is intended to provide a product stream enriched in high octane paraffin isomers from a feed stream comprised of normal and singly branched $C_4$ to $C_7$ paraffins by the selective addition of branching into the molecular structure of the feed stream paraffins. Hydroisomerization ideally will achieve high conversion levels of the normal and singly branched light paraffins to more highly branched paraffins while at the same time minimizing the conversion by cracking. Hydroisomerization can be achieved by contacting the feed with a hydroisomerization catalyst in an isomerization zone under hydroisomerizing conditions.

"Zeolite" shall mean not only materials containing silicon atoms and, optionally, aluminum atoms in the crystalline lattice structure thereof, but also materials which contain suitable replacement atoms for such silicon and aluminum atoms. Zeolites can include (a) intermediate and (b) final or target zeolites produced by (1) direct synthesis or (2) post-crystallization treatment (secondary synthesis). Secondary synthesis techniques allow for the synthesis of a target zeolite from an intermediate zeolite using techniques such as heteroatom lattice substitution techniques and acid leaching. For example, an aluminosilicate can be synthesized from an intermediate borosilicate by post-crystallization heteroatom lattice substitution of boron for aluminum. Such techniques are known in the art (see, e.g., U.S. Pat. No. 6,790,433).

"STI-type zeolite" refers to a zeolite having the STI framework topology, as classified by the Structure Commission of the International Zeolite Association according to the rules of the IUPAC Commission on Zeolite Nomenclature. STI-type zeolites possess a two-dimensional channel system delineated by 10-membered rings (free dimensions 4.7×5.0 Å) connected through 8-membered rings (2.7×5.6 Å). Examples of STI-type zeolites include the zeolites designated "SSZ-75" and "TNU-10." In one embodiment, the STI-type zeolite has a silica to alumina mole ratio of at least 15. It should be noted that the phrase "mole ratio of at least 15" includes the case where there is no aluminum oxide, i.e., the mole ratio of silicon oxide to aluminum oxide is infinity. In that case, the zeolite is comprised of essentially all silicon oxide.

"$C_n$" describes a hydrocarbon molecule wherein "n" denotes the number of carbon atoms in the molecule.

"Paraffin" refers to any saturated hydrocarbon compound, i.e., a hydrocarbon having the formula $C_nH_{(2n+2)}$ where n is a positive non-zero integer.

"Normal paraffin" refers to a saturated straight chain hydrocarbon.

"Singly branched paraffin" refers to a saturated hydrocarbon having the molecular structure

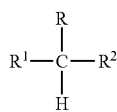

where R, $R^1$ and $R^2$ are independent alkyl groups; and wherein R is an alkyl group (e.g., methyl) as a branch and $R^1$ and $R^2$ represent portions of the paraffin chain or backbone.

"Doubly branched paraffin" refers to a saturated hydrocarbon such as

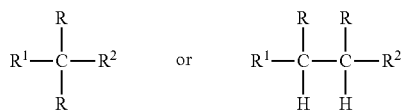

where R, $R^1$ and $R^2$ are independent alkyl groups; and wherein R is an alkyl group (e.g., methyl) as a branch and $R^1$ and $R^2$ represent portions of the paraffin chain or backbone. Thus, a singly branched paraffin has one R group per paraffin molecule while a doubly branched paraffin has two R groups per molecule where the two R groups can be the same alkyl groups or different ones.

"Mono-methylpentane" refers to 2-methylpentane, 3-methylpentane, or mixtures of these isomers. Similarly, "dimethylbutane" refers to 2,2-dimethylbutane, 2,3-dimethylbutane, or mixtures of these isomers.

The isomers of $C_4$ to $C_6$ paraffins are included in the light naphtha fraction of the gasoline pool. One skilled in the art will recognize that some isomers of $C_7$ paraffin can also be present in the light naphtha fraction. However, heptane and its isomers are generally present only in minor amounts.

When used herein, the Periodic Table of the Elements refers to the version published by CRC Press in the *CRC Handbook of Chemistry and Physics*, 88th Edition (2007-2008). The names for families of the elements in the Periodic Table are given here in the Chemical Abstracts Service (CAS) notation.

Feed Stream

A refinery feed stream referred to as light paraffins typically comprises mainly normal and singly branched $C_4$ to $C_7$ hydrocarbons and has a relatively low octane number because it contains substantial amounts of $C_4$ to $C_6$ normal paraffins. Typically, the feed stream has a RON of less than 80 (e.g., less than 75, 70, 65, 60, or 55).

In one embodiment, the feed stream comprises predominantly normal and singly branched $C_4$ to $C_6$ paraffins. The singly branched $C_4$ to $C_6$ paraffins can be singly branched $C_5$ to $C_6$ paraffins. Generally, the feed stream comprises at least 10 wt. % $C_4$ to $C_6$ normal paraffins (e.g., at least 20 wt. %, 30 wt. %, 40 wt. %, 50 wt. %, 60 wt. %, 70 wt. %, 80 wt. %, or 90 wt. % $C_4$ to $C_6$ normal paraffins). In another embodiment, the feed stream comprises predominantly normal and singly branched $C_5$ to $C_6$ paraffins. In yet another embodiment, the feed stream comprises at least 10 wt. % n-hexane (e.g., at least 20 wt. %, 30 wt. %, 40 wt. %, 50 wt. %, 60 wt. %, 70 wt. %, 80 wt. %, or 90 wt. % n-hexane). As used herein, the term "predominantly" means an amount of 50 wt. % or more of the substance in question as a fraction of the total feed.

Optionally, the feed can be hydrotreated in a hydrotreating process to remove any excess sulfur and/or nitrogen content, prior to the hydroisomerization process. Optionally, the feed contains benzene which can be hydrogenated to cyclohexane in the hydroisomerization process to reduce the benzene content in the gasoline product.

Hydroisomerization Catalyst

Catalysts useful for hydroisomerization processes are generally bifunctional catalysts that include a hydrogenation/dehydrogenation component and an acidic component. The hydroisomerization catalyst usually comprises at least one Group VIII metal, (e.g., platinum or palladium) on a porous inorganic oxide support (e.g., alumina, silica-alumina or a zeolite). If the support itself does not have sufficient acidity to promote the needed isomerization reactions, such acidity can be added. Examples of a useful acid component include a zeolite, a halogenated alumina component, or a silica-alumina component.

Catalysts useful for hydroisomerization processes described herein comprise at least one Group VIII metal on an STI-type zeolite, typically in the aluminosilicate form. The zeolite SSZ-75 has the STI framework topology. SSZ-75 and methods for making it are disclosed in U.S. Pat. No. 7,713,512. The at least one Group VIII metal compound can be present in an amount to provide sufficient activity for the catalyst to have commercial use. By Group VIII metal compound, as used herein, is meant the metal itself or a compound thereof. Non-limiting examples of Group VIII metals include platinum, palladium, and combinations thereof.

The at least one Group VIII metal can be combined with or incorporated into the STI-type zeolite by any one of numerous procedures, for example, by co-milling, impregnation, or ion exchange. Processes which are suitable for these purposes are known to those skilled in the art. The at least one Group VIII metal can be present in the STI-type zeolite in an amount suitable for catalysis of light paraffins. The metal-loaded zeolite catalyst can be sufficiently active and selective under hydroisomerization conditions so as to provide a substantial increase in high octane doubly branched light paraffins during a single pass through a hydroisomerization zone or reactor. Generally, the amount of metal component combined with the zeolite can be in the range from 0.05 wt. % to 5.0 wt. % (e.g., from 0.1 wt. % to 3.0 wt. %, or from 0.1 wt. % to 1.0 wt. %) wherein the given wt. % is based on the weight of the zeolite.

Other metals, such as transition metals of Group VIIB (e.g., rhenium) and Group IIIA to Group VA metals (e.g., gallium, indium, germanium, tin and/or lead) can also be combined with the zeolite, in addition to the Group VIII metal. Such metals can be combined with the zeolite in amounts generally within the same range as given hereinabove with respect to Group VIII metals.

Optionally, the catalyst can be pre-sulfided to lower the hydrogenolysis activity. Procedures that are suitable for pre-sulfiding metal-loaded zeolite catalysts are known to those skilled in the art.

In situations where the catalyst is deactivated by coke deposit or other poisons, the catalyst activity can be rejuvenated via catalyst regeneration. Procedures suitable for the regeneration of zeolite catalysts are known in the art. In addition, the zeolite catalyst is environmentally benign since it is not chlorinated to boost its acidity.

Catalysts based on the STI-type zeolites described herein have high levels of activity for the hydroisomerization of light paraffins and also show high selectivity in the conversion of n-hexane to the higher octane $C_6$ isomer 2,3-dimethylbutane over the lower octane $C_6$ isomer 2,2-dimethylbutane.

Process Conditions

The catalytic hydroisomerization conditions employed depend on the feed used for the hydroisomerization and the desired properties of the product. Typical hydroisomerization conditions which can be employed include a temperature of from 150° F. to 700° F. (66° C. to 371° C.), e.g., 400° F. to 650° F. (204° C. to 343° C.), 450° F. to 600° F. (232° C. to 316° C.), or 475° C. to 515° C. (246° C. to 268° C.); a pressure of from 50 psig to 2000 psig (0.34 MPa to 13.79 MPa), e.g., 100 psig to 1000 psig (0.69 MPa to 6.89 MPa), or 150 psig to 400 psig (1.03 MPa to 2.76 MPa); a hydrocarbon feed liquid hourly space velocity (LHSV) of from 0.5 $h^{-1}$ to 5 $h^{-1}$, e.g., 0.5 $h^{-1}$ to 3 $h^{-1}$, or 0.75 $h^{-1}$ to 2.5 $h^{-1}$; and a hydrogen to hydrocarbon ($H_2$/HC) mole ratio of from 0.5 to 10, e.g., 1 to 10, or 2 to 8. Exemplary hydroisomerization conditions include a temperature of from 475° F. to 515° F. (246° C. to 268° C.), a pressure of from 150 psig to 400 psig (1.03 MPa to 2.76 MPa), a LHSV of from 0.5 $h^{-1}$ to 3 $h^{-1}$, and a $H_2$/HC mole ratio of from 2 to 8.

In one embodiment, the hydroisomerization conditions can include a temperature at or about the temperature for maximum isomer yield of one or more light paraffins. The temperature for maximum isomer yield from a particular feed stream (e.g., comprising one or more light normal paraffins) can be determined empirically for a given zeolite catalyst, e.g., by performing hydroisomerization of the feed stream over a range of temperatures under defined conditions, and analyzing the composition of the product stream for each hydroisomerization temperature. The product analysis can be conducted, for example, by on-line GC analysis. Hydroisomerization temperatures can be successively increased, e.g., in 5° F. to 10° F. (2.8° C. to 5.6° C.) increments from a starting hydroisomerization temperature (e.g., about 400° F., 204° C.), until isomer yields in the product stream from the reactor have peaked. Naturally, the temperature for maximum isomer yield can vary depending on the composition and activity of the zeolite catalyst, and on other factors.

In some embodiments, where the conversion of the hydrocarbon feedstock is lower than targeted, or the yield of the preferred product, e.g., 2,3-dimethylbutane, is lower than targeted, the process can optionally include a separation stage for recovering at least a portion of the unconverted feedstock. Optionally, at least a portion of the feed stream including any unconverted feedstock can be recycled to the hydroisomerization unit or zone.

The hydroisomerization of light paraffins can be performed in a hydroisomerization zone or reactor. Various reactor types can be used. For example, a hydrocarbon feed (e.g., containing substantial amounts of light paraffins) can be contacted with the zeolite catalyst in a fixed bed system, a moving bed system, a fluidized system, a batch system, or combinations thereof. In a fixed bed system, the preheated feed is passed into at least one reactor that contains a fixed bed of the catalyst prepared from material comprising the zeolite catalyst. The flow of the feed can be upward, downward or radial. The reactors can be equipped with instrumentation to monitor and control temperatures, pressures, and flow rates. Multiple beds can also be used, wherein two or more beds can each contain a different catalytic composition, at least one of which can comprise an STI-type zeolite.

In one embodiment, the feed stream can be contacted with the zeolite catalyst during a single pass of the feed stream through the hydroisomerization zone or reactor to provide an isomerized product at maximum isomer yield comprising at least 9 mole % of dimethylbutane.

Products

The hydroisomerization processes described herein yield an isomerized product enriched in more highly branched $C_4$ to $C_7$ paraffins, and primarily branched $C_5$ to $C_6$ isomers at maximum isomer yield.

In one embodiment, the isomerized product generally comprises at least 9 mole % of dimethylbutane. In a sub-embodiment, the isomerized product comprises at least 5 mole % of 2,3-dimethylbutane (e.g., at least 6 mole %, at least 7 mole %, at least 8 mole %, or at least 9 mole % of 2,3-dimethylbutane).

In one embodiment, the isomerized product comprises 2,2-dimethylbutane and 2,3-dimethylbutane and has a 2,3-dimethylbutane to 2,2-dimethylbutane mole ratio of at least 1 (e.g., from 1 to 100), at least 5 (e.g., from 5 to 100), at least 10 (e.g., from 10 to 100), or at least 15 (e.g., from 15 to 100). The isomerized product can further comprise 2-methylpentane and 3-methylpentane.

In one embodiment, the isomerized product has an RON of at least 85 (e.g. at least 90 or 95).

EXAMPLES

The following illustrative examples are intended to be non-limiting.

Example 1

Preparation of Hydroisomerization Catalyst

Calcined aluminosilicate SSZ-75 (Al-SSZ-75) having a $SiO_2/Al_2O_3$ mole ratio of 30 (prepared as described in U.S. Pat. No. 7,713,512) was ion exchanged with an aqueous $(NH_3)_4Pt(NO_3)_2$ solution to load the zeolite with 0.5 wt. % Pt. The resulting catalyst was subsequently calcined by heating in air at 700° F. for 5 hours. The Pt-loaded zeolite was reduced with hydrogen prior to hydroisomerization studies.

Example 2

Hydroisomerization of n-Hexane Over Pt-Exchanged Al-SSZ-75

The catalytic hydroisomerization of n-hexane was carried out using the Al-SSZ-75 catalyst of Example 1 in a flow type fixed bed reactor with pure n-hexane as feed, at a temperature corresponding to the maximum isomer yield for the catalyst. The temperature for maximum isomer yield for the catalyst was determined by product analysis (on-line GC) over a range of successively increased temperatures (10° F. increments) starting at a temperature of 400° F., until isomer yields in the product stream of the catalyst sample reached a maximum. The temperature for maximum isomer yield for the catalyst is presented in Table 2. The hydroisomerization conditions included a pressure of 200 psig, a LHSV of 1 $h^{-1}$, and a molar $H_2$ to hydrocarbon ratio of 6:1. The reaction products were analyzed with an on-line GC to quantify each of the $C_6$ alkane isomers, and the results are set forth in Table 2.

Example 3

Hydroisomerization of n-Hexane Over Pd-Exchanged Zeolite Y, Mordenite, ZSM-5 and SSZ-32

The hydroisomerization of n-hexane was carried out over Pd/Y, Pd/mordenite, Pd/ZSM-5 and Pd/SSZ-32 in a flow type fixed bed reactor with pure n-hexane as feed at the temperature, pressure, LHSV, and molar $H_2$ to hydrocarbon ratio as described in Example 2. These catalysts were prepared as described in Example 1 for Pt/Al-SSZ-75. The results at the respective temperatures corresponding to maximum isomer yield are also set forth in Table 2.

TABLE 2

| Catalyst | Zeolite Properties | Temp @ Max. Isomer Yield, °F | Max. Isomer Yield, mol. % | Distribution of $C_6$ Isomers (excluding n-hexane), mol. % | | | |
|---|---|---|---|---|---|---|---|
| | | | | 2,2-dimethyl-butane | 2,3-dimethyl-butane | 2-methyl-pentane | 3-methyl-pentane |
| Pt/SSZ-75 | 10/8MR/2D | 490 | 63.8 | 0.6 | 9.1 | 55.0 | 35.4 |
| Pd/Y | 12-MR/3D | 580 | 79.5 | 21.9 | 10.0 | 41.2 | 27.0 |
| Pd/Mordenite | 12/8-MR/1D | 560 | 78.6 | 21.5 | 10.8 | 40.7 | 27.0 |
| Pd/ZSM-5 | 10-MR/3D | 500 | 74.4 | 0.2 | 3.0 | 59.6 | 37.2 |
| Pd/SSZ-32 | 10-MR/1D | 580 | 68.5 | 0.1 | 2.1 | 59.0 | 38.9 |

In the hydroisomerization of n-hexane with an STI-type zeolite catalyst, the highest octane 2,3-dimethylbutane isomer was preferentially formed with about 65 mole % conversion of the n-hexane with less than 15 mole % cracking. The results demonstrate that using the catalysts based on STI-type zeolites advantageously provide selectivity to the highest octane $C_6$ isomer, namely 2,3-dimethylbutane rather than the lower octane 2,2-dimethylbutane. Although ZSM-5 and SSZ-32 gave high 2,3-dimethylbutane to 2,2-dimethylbutane mole ratios, the total dimethylbutane produced during n-hexane hydroisomerization by these zeolites was very small (3.2 and 2.2 mole %, respectively, at maximum isomer yield), as compared with the total dimethylbutane production by SSZ-75.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. A hydroisomerization process, comprising: contacting a hydrocarbon feed stream comprising predominantly normal and singly branched C4 to C7 paraffins and at least 10 wt. % n-hexane, under hydroisomerization conditions, with a catalyst comprising an aluminosilicate zeolite SSZ-75 and at least one Group VIII metal selected from the group consisting of platinum, palladium, and combination thereof to form an isomerized product having a higher concentration of doubly and singly branched paraffins than the feed stream and having a 2,3-dimethylbutane to 2,2-dimethylbutane mole ratio of at least 1.

2. The process of claim 1, wherein the feed stream has a RON of less than 75.

3. The process of claim 1, wherein the feed stream comprises predominantly normal and singly branched $C_4$ to $C_6$ paraffins.

4. The process of claim 1, wherein the feed stream comprises predominantly normal and singly branched $C_5$ to $C_6$ paraffins.

5. The process of claim 1, wherein the feed stream comprises at least 50 wt. % n-hexane.

6. The process of claim 1, wherein the hydroisomerization conditions comprise a temperature of from 400° F. to 650° F. (204° C. to 343° C.), a pressure of from 50 psig to 2000 psig (0.34 MPa to 13.79 MPa), a hydrocarbon feed LHSV of from 0.5 $h^{-1}$ to 5 $h^{-1}$, and a hydrogen to hydrocarbon ($H_2$/HC) mole ratio of from 0.5 to 10.

7. The process of claim 1, wherein the catalyst comprises 0.05 wt. % to 5 wt. % of the at least one Group VIII metal, based on the weight of the zeolite.

8. The process of claim 1, wherein the isomerized product comprises at least 9 mole % of dimethylbutane.

9. The process of claim 1, wherein the isomerized product has a 2,3-dimethylbutane to 2,2-dimethylbutane mole ratio of at least 5.

10. The process of claim 1, wherein the isomerized product has a RON of at least 85.

* * * * *